(12) United States Patent
Wang et al.

(10) Patent No.: US 7,942,050 B2
(45) Date of Patent: May 17, 2011

(54) RELIABILITY TEST PLATE FOR APPEARANCE TREATMENT AND THE METHOD THEREOF

(75) Inventors: Chung-Ming Wang, Taipei (TW); Yuan Yu, Taipei (TW)

(73) Assignee: Pegatron Corporation, Taipei (TW)

( * ) Notice: Subject to any disclaimer, the term of this patent is extended or adjusted under 35 U.S.C. 154(b) by 747 days.

(21) Appl. No.: 11/972,807

(22) Filed: Jan. 11, 2008

(65) Prior Publication Data

US 2008/0173068 A1    Jul. 24, 2008

(30) Foreign Application Priority Data

Jan. 18, 2007  (TW) ............................... 96101951 A

(51) Int. Cl.
*G01B 21/08* (2006.01)
(52) U.S. Cl. .................................................. 73/150 R
(58) Field of Classification Search .................. None
See application file for complete search history.

(56) References Cited

U.S. PATENT DOCUMENTS

| | | | | | |
|---|---|---|---|---|---|
| 2,715,830 | A | * | 8/1955 | Lewis et al. | 73/1.89 |
| 2,829,517 | A | * | 4/1958 | Kushner | 73/150 R |
| 3,059,463 | A | * | 10/1962 | Lappala et al. | 73/7 |
| 3,289,241 | A | * | 12/1966 | Garrison et al. | 401/266 |

* cited by examiner

*Primary Examiner* — Robert R Raevis
(74) *Attorney, Agent, or Firm* — Thomas, Kayden, Horstemeyer & Risley

(57) ABSTRACT

The reliability test plate for appearance treatment is used to coat with predetermined paint or material. The reliability test plate at least includes an appearance simulation area for simulating at least partial appearance of an electronic product, and at least one test plane area. The appearance simulation area and the test plane area can be coated with the predetermined paint. Then, one reliability test item can be performed at the test plane area.

18 Claims, 2 Drawing Sheets

RELIABILITY TEST PLATE FOR APPEARANCE TREATMENT AND THE METHOD THEREOF

RELATED APPLICATIONS

This application claims priority to Taiwan Application Serial Number 96101951, filed Jan. 18, 2007, which is herein incorporated by reference.

BACKGROUND OF THE INVENTION

1. Field of the Invention

The invention relates to a test plate and, more particularly, to a reliability test plate for appearance treatment.

2. Description of the Related Art

Along with the communication for information becomes more popular, the usage frequency of various portable devices increases day by day, so that portable devices have been accessories which are necessarily carried about by users. Commonly, when a user buys a portable product, the function of the product is not the only aspect which is considered, and the appearance design is the key aspect which affects the user to determine whether to buy or not when products almost have the same functions. Therefore, during the development of products, different color matching and appearance treatment should be tried.

Commonly, after designs for the portable products are finished, appearances of the products are formed by processes of developing a mold, injection molding to form outer housing members, painting, plating and so on. However, along with new materials for outer housing are continuously developed, the fit between the new materials and the used paint has been one bottleneck of the development schedule and the development cost of the portable devices. Conventionally, since the spraying paint test can only be performed after the whole mold is developed and the outer housing members are formed by injection molding, once the fit between the appearance design and the used paint is bad, the problem can be solved only by changing the paint or modifying the appearance design. But the above processes will cause to re-make a mold or to re-choose the paint, which will consume time and prolong the whole development schedule.

Therefore, how to shorten the development schedule has been the main objective for engineers.

BRIEF SUMMARY OF THE INVENTION

One objective of the invention is to provide a test plate for reliability analysis of each type of appearance treatment (painting, plating, etc.).

Another objective of the invention is to provide a reliability test plate which can make the reliability analysis of paint be performed before a mold is developed.

Another objective of the invention is to provide a reliability test method which can make the reliability analysis of paint done before a mold is developed.

According to the above objectives, the invention provides a paint reliability test plate for coating with predetermined paint, and the test plate at least includes an appearance simulation area whose surface simulates at least partial appearance shape of an electronic product, and at least a test plane area, wherein the appearance simulation area and the test plane area can be coated with the predetermined paint, and a reliability test item can be performed at the test plane area.

In one embodiment, the appearance simulation area at least includes a curved surface area which is formed with squares which are arranged to form a matrix shape, and a slope angle area which is formed with a plurality of chevron bars which are arranged in parallel. According to another embodiment, the invention provides a paint reliability test method for forecasting the effect of coating the outer housing of an electronic product with the predetermined paint, and the test method at least includes the steps of providing a reliability test plate which includes an appearance simulation area simulating the appearance of the electronic product and at least a test plane area, coating the appearance simulation area and the test plane area with the predetermined paint, and performing a reliability test item at the test plane area.

In one embodiment, the appearance simulation area further includes a curved surface area which is formed with squares which are arranged to form a matrix shape, and a slope angle area which is formed with a plurality of chevron bars which are arranged in parallel.

To sum up, since the manufacturer of outer housing of the invention is unnecessary to make a mold first, the cost and the time for making a mold are saved. In addition, if the material of the paint needs to be adjusted, the paint provider can directly adjust, which is different from the conventional manufacture process in which the paint manufacturer does corresponding adjustment after the manufacturer of outer housing finishes testing and sends a test result to the paint manufacturer.

BRIEF DESCRIPTION OF THE SEVERAL VIEWS OF THE DRAWINGS

These and other features, aspects, and advantages of the present invention will become better understood with regard to the following description, appended claims, and accompanying drawings.

DETAILED DESCRIPTION OF THE EMBODIMENTS

A conventional reliability analysis between paint and an outer housing is done only after a mold is developed, outer housing members are formed by injection molding and paint is sprayed. However, once the test result is poor, it needs to re-make a mold or re-choose paint, which delays the whole develop schedule. Therefore, the invention utilizes a reliability test plate to simulate all possible appearances of portable devices, and the reliability test plate is coated with the chosen paint first, and then the reliability test can be directly performed at the reliability test plate, and the choice of paint or a little adjustment of the appearance can be performed according to the test result. After the test result satisfies a standard, the mold of the outer housing is developed, which avoids unnecessarily re-working and shortens the whole manufacture schedule. The following takes an embodiment to illustrate the application of the invention, but the application of the invention is not limited to the following embodiment or a portable device.

Figure 1:
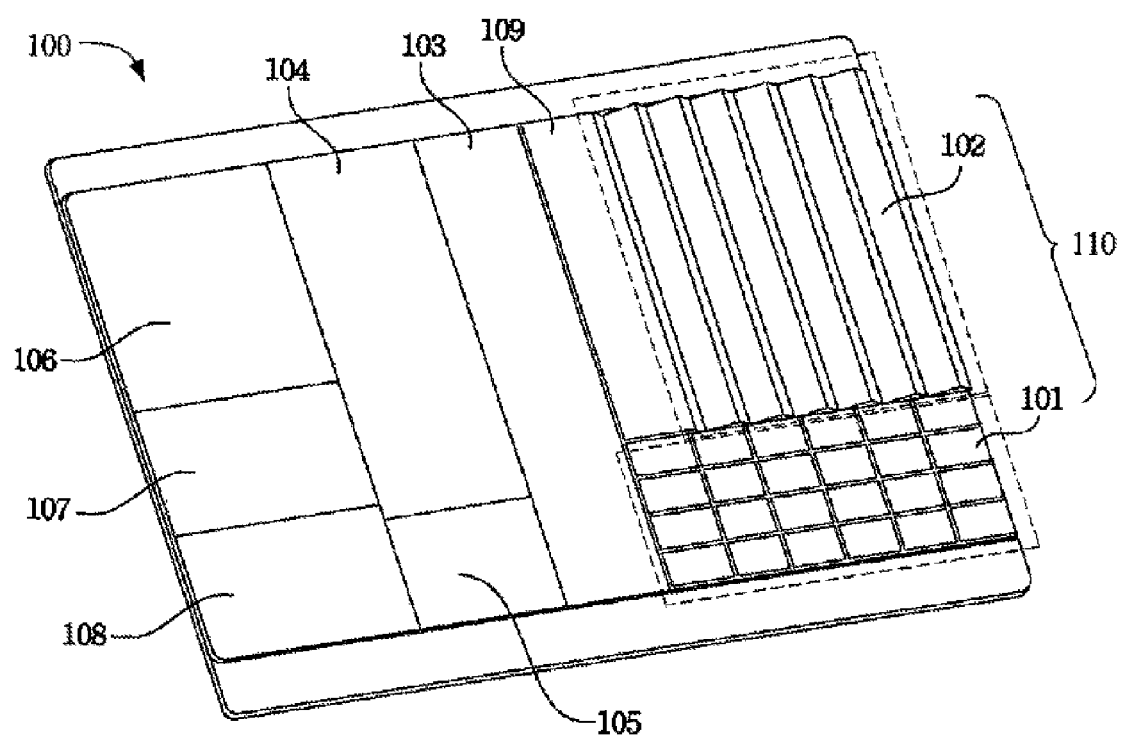
FIG. 1 is skeleton diagram showing a reliability test plate according to an embodiment of the invention.

FIG. 1 is a skeleton diagram showing a reliability test plate according to an embodiment of the invention. According to the embodiment, an appearance simulation area 110 for simulating the possible appearance of a portable device and a plurality of plane areas 103~109 are formed on a reliability test plate 100. Wherein the appearance simulation area 110 at least includes a curved surface area 101 and a slope angle area 102. The material forming the reliability test plate 100 can be changed according to the material of the outer housing of the portable device which is simulated. For example, if the material of the outer housing of the portable device which is simulated is magnesium, and then the reliability test plate 100 is also formed by magnesium. In the embodiment, the volume of the reliability test plate 100 is about 11.4 centimeters×7.5 centimeters×0.4 centimeter.

Wherein the curved surface area 101 is formed with squares which are arranged to form a matrix shape, and the appearance of each square is similar to a key of a portable device, but each square has a different degree of surface curvature to simulate the effect of the possible presenting degree of color and luster, the homogeneous degree, the adhesion degree, the abrasion resistance of the paint and so on after the paint is used to coat.

The slope angle area 102 is formed with a plurality of chevron bars which are arranged in parallel, and each chevron bar has a round angle (R angle) with different angle to simulate possible turning angles of the appearance of an electronic product. The abrasion resistance degree of the paint on different turning angles can be simulated via the slope angle area 102.

The plurality of plane areas 103-109 are used for different tests after the reliability test plate 100 is coated with paint. In other words, the number of the plane areas which are obtained by cutting the reliability test plate 100 is related to the number of the test items, and the size of each plane area is related to the test item which will be performed thereon. In the embodiment, the paint test items for a portable device include an alcohol erosion test performed on a plan area 103 whose size is 1.5 centimeters×6.5 centimeters, a hardness test performed on a plan area 104 whose size is 2 centimeters×5 centimeters, an abrasion resistance test performed on a plan area 105 whose size is 2 centimeters×1.5 centimeters, an adhesiveness test performed on a plan area 106 whose size is 3 centimeters×3 centimeters, a hand sweat test performed on a plan area 107 whose size is 3 centimeters×1.75 centimeters, an corrosion resistance test for special chemical material performed on a plane area 108 whose size is 3 centimeters×1.75 centimeters, and an abrasion resistance test performed on a plan area 109 whose size is 1 centimeter×6.5 centimeters. However, the above test items and the sizes of the plane areas can be changed according to users' requirements. For example, if more than six test items need to be performed, the number of the plane areas can be increased by further cutting, or if the test item needs a larger plan area, the users can expand the whole area of the reliability test plate 100.

Figure 2:
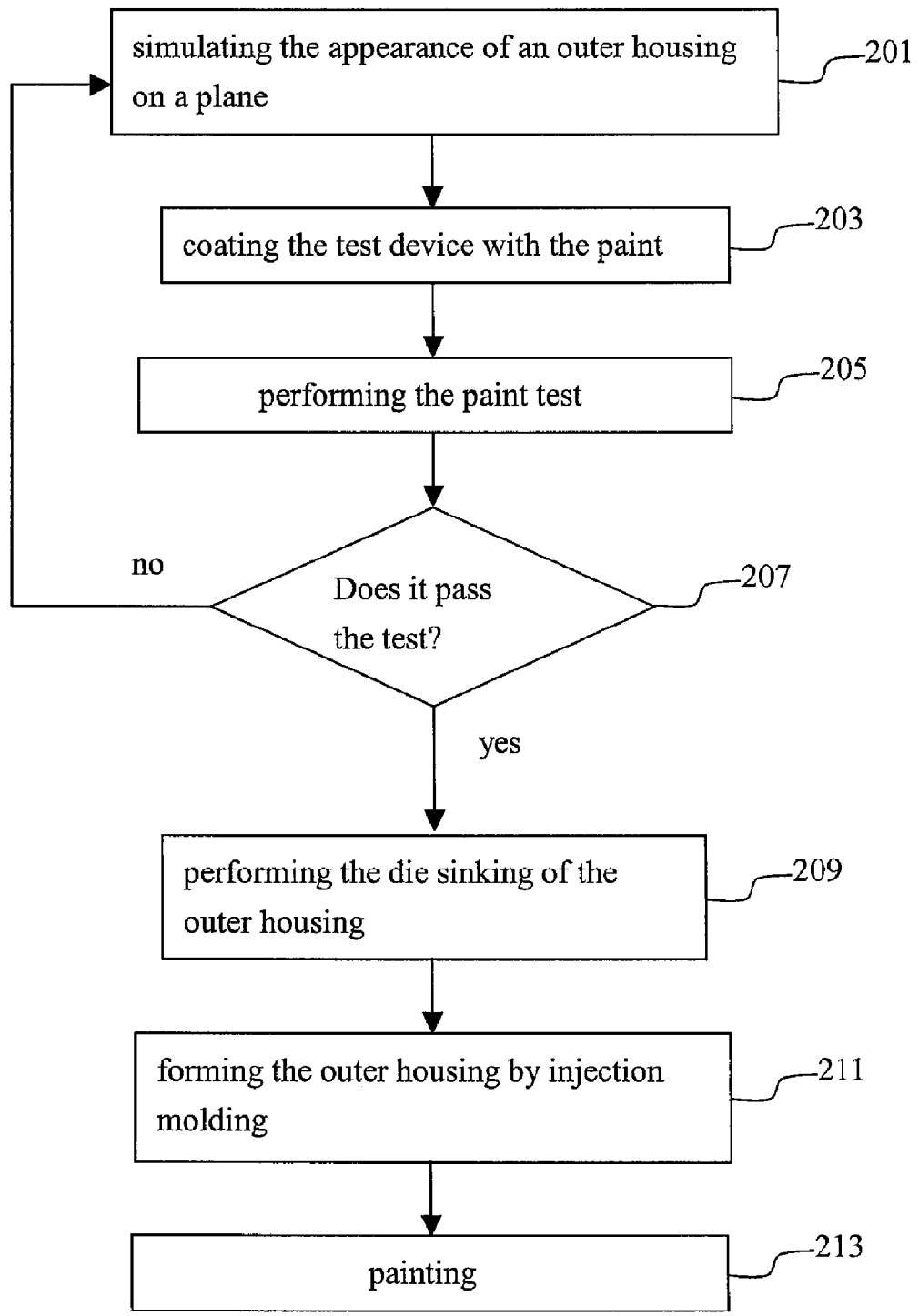
FIG. 2 is a manufacture flow chart showing how to coat an outer housing with paint by a reliability test plate of the invention.

FIG. 2 is a manufacture flow chart showing how to coat an outer housing with paint by a reliability test plate of the invention. Please refer to FIG. 1 and FIG. 2. First, in step 201, the appearance of an outer housing is simulated on a plane plate to form a reliability test plate 100, wherein the material which is used to form the reliability test plate 100 can be changed according to the material of the simulated outer housing. The reliability test plate 100 includes at least a curved surface area 101 which simulates the undulation of an outer housing, a slope angle area 102 which simulates a turning angle of the outer housing and at least a test plane area, wherein the number of the plane area is related to the number of the test items which will be performed, and the sizes of the plane areas are related to the test items which will be performed. Next, in step 203, the reliability test plate 100 is coated with the predetermined paint. Step 205 follows after the painting is finished, and each predetermined test item such as the alcohol erosion test, the hardness test of the paint, the abrasion resistance test of the paint or the adhesiveness test of the paint is performed at the paint on the reliability test plate 100. After the predetermined test items are finished, the test result is determined in step 207, if the test result does not satisfy an established requirement, the predetermined paint is fine adjusted, or it returns to step 201, the manufacturer of outer housing adjusts the appearance and a corresponding reliability test plate is formed again, and then steps 203 to 207 are repeated. If the test result satisfies the established requirement, the manufacturer of outer housing can make a mold in step 209. In step 211, the outer housing is formed by the injection molding, and finally, the outer housing is coated with paint in step 213.

The invention is not limited to the test of paint, and can also be applied in other appearance treatment such as a plating process. In the embodiment of the plating process, only the above step of coating with the predetermined paint needs to be changed to be performing a predetermined plating process, and the reliability test plate can still be used, and test items of the reliability test can be changed according to the requirement of the plating process.

According to the flow path of the invention, the above steps 203 to 207 can be performed by a paint provider. In other words, the manufacturer of outer housing only needs to provide a reliability test plate which is formed according to the appearance and the material of the outer housing to the paint provider who will perform each type of test processes after the reliability test plate is coated with the appointed paint. If the test result does not satisfy a requirement, the predetermined paint is fine adjusted by the paint provider, or the appearance is adjusted by the manufacturer of the outer housing to form a corresponding reliability test plate again, and the reliability test plate is provided to the paint provider to repeat the above steps 203 to 207 until the test result satisfies the requirement. Along the flow path of the invention, the manufacturer of outer housing is unnecessary to antecedently make a mold, so that the cost and the time of die sinking can be saved. In addition, if the material of the paint needs to be adjusted, the paint provider can directly adjust, which is different from the conventional manufacture process in which the paint manufacturer performs a corresponding adjustment after the manufacturer of outer housing finishes testing and sends a test result to the paint manufacturer.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A reliability test plate for a reliability test of appearance treatment, the test plate comprising:
    an appearance simulation area, the surface of the appearance simulation area simulating partial appearance shape of an electronic product, the appearance simulation area including a curved surface area for simulating the appearance undulation of the electronic product; and
    a plane area, wherein the appearance treatment is capable of being performed at the appearance simulation area and the plane area, and the reliability test is capable of being performed at the plane area.

2. The reliability test plate according to claim 1, wherein the curved surface area is formed with squares which are arranged to form a matrix shape.

3. The reliability test plate according to claim 2, wherein each of the squares has a different degree of surface curvature.

4. The reliability test plate according to claim 1, wherein the appearance simulation area further comprises:
a slope angle area for simulating a turning angle of the appearance of the electronic product.

5. The reliability test plate according to claim 4, wherein the slope angle area is formed with a plurality of chevron bars which are arranged in parallel.

6. The reliability test plate according to claim 5, wherein each of the chevron bars has a different turning angle.

7. The reliability test plate according to claim 1, wherein the appearance treatment is a painting process.

8. The reliability test plate according to claim 1, wherein the appearance treatment is a plating process.

9. The reliability test plate according to claim 1, wherein the reliability test is one or combination of an alcohol erosion test, a hardness test, an abrasion resistance test, an adhesiveness test and a corrosion resistance test.

10. A reliability test method for forecasting the effect of performing an appearance treatment on the outer housing of an electronic product, the test method comprising:
providing a reliability test plate which comprises an appearance simulation area simulating the outer housing of the electronic product and at least a plane area, the appearance simulation area including a curved surface area for simulating the appearance undulation of the electronic product;
performing the appearance treatment on the appearance simulation area and the plane area; and
performing a reliability test at the plane area.

11. The reliability test method according to claim 10, wherein the appearance treatment is a painting process.

12. The reliability test method according to claim 10, wherein the appearance treatment is a plating process.

13. The reliability test method according to claim 10, wherein the curved surface area is formed with squares which are arranged to form a matrix shape.

14. The reliability test method according to claim 13, wherein each of the squares has a different degree of surface curvature.

15. The reliability test method according to claim 10, wherein the appearance simulation area further comprises:
a slope angle area for simulating a turning angle of the appearance of the electronic product.

16. The reliability test method according to claim 15, wherein the slope angle area is formed with a plurality of chevron bars which are arranged in parallel.

17. The reliability test method according to claim 16, wherein each of the chevron bars has a different turning angle.

18. The reliability test method according to claim 10, wherein the reliability test is one or combination of an alcohol erosion test, a hardness test, an abrasion resistance test, an adhesiveness test and a corrosion resistance test.

* * * * *